(12) United States Patent
Cohen et al.

(10) Patent No.: US 11,291,391 B2
(45) Date of Patent: Apr. 5, 2022

(54) IMPLANTABLE OCULAR GLUCOSE SENSOR DEVICES AND METHODS

(71) Applicant: MicroOptx Inc., Maple Grove, MN (US)

(72) Inventors: Edward Aaron Cohen, Columbia Heights, MN (US); Roy Christian Martin, Maple Grove, MN (US)

(73) Assignee: MicroOptx Inc., Maple Grove, MN (US)

( * ) Notice: Subject to any disclaimer, the term of this patent is extended or adjusted under 35 U.S.C. 154(b) by 330 days.

(21) Appl. No.: 16/209,010

(22) Filed: Dec. 4, 2018

(65) Prior Publication Data

US 2019/0175083 A1    Jun. 13, 2019

Related U.S. Application Data

(60) Provisional application No. 62/597,156, filed on Dec. 11, 2017.

(51) Int. Cl.
*A61B 5/145* (2006.01)
*A61B 5/00* (2006.01)
(Continued)

(52) U.S. Cl.
CPC ............ *A61B 5/14532* (2013.01); *A61B 5/03* (2013.01); *A61B 5/14735* (2013.01);
(Continued)

(58) Field of Classification Search
CPC ...... A61B 2562/0247; A61B 2562/166; A61B 3/16; A61B 5/0031; A61B 5/03;
(Continued)

(56) References Cited

U.S. PATENT DOCUMENTS 6,120,460 A * 9/2000 Abreu ................. A61B 3/1241
600/405
6,181,957 B1    1/2001 Lambert et al.
(Continued)

FOREIGN PATENT DOCUMENTS

WO    WO 00/30534    6/2000
WO    WO 2001/16575    3/2001
(Continued)

OTHER PUBLICATIONS

Huang et al., "LC Passive Wireless Sensors Toward a Wireless Sensing Platform: Status, Prospects, and Challenges" Oct. 5, 2016.
(Continued)

*Primary Examiner* — Sean P Dougherty
*Assistant Examiner* — Alexander H Connor
(74) *Attorney, Agent, or Firm* — Fish & Richardson P.C.

(57) ABSTRACT

Monitoring glucose concentration in aqueous humor can include inserting an implantable device into an eye and determining glucose concentration as a function of glucose sensed at the implantable device. In some implantable device embodiments, the device includes a polymer layer comprising a material that changes volume in response to varying glucose concentrations of the aqueous humor. A pressure sensor in the device can detect the changes in volume. In some implantable device embodiments, the device includes electrodes for determining the glucose concentration.

21 Claims, 3 Drawing Sheets

(51) Int. Cl.
*A61B 5/03* (2006.01)
*A61B 5/1473* (2006.01)
*A61B 3/16* (2006.01)
*G02C 7/04* (2006.01)

(52) U.S. Cl.
CPC ............ *A61B 5/686* (2013.01); *A61B 5/6821* (2013.01); *A61B 5/6867* (2013.01); *A61B 3/16* (2013.01); *A61B 5/0031* (2013.01); *A61B 2562/0247* (2013.01); *A61B 2562/166* (2013.01); *G02C 7/04* (2013.01)

(58) Field of Classification Search
CPC ............ A61B 5/14532; A61B 5/14735; A61B 5/6821; A61B 5/686; A61B 5/6867; G02C 7/04
See application file for complete search history.

(56) References Cited

U.S. PATENT DOCUMENTS

| | | | |
|---|---|---|---|
| 6,268,161 B1 | 7/2001 | Han et al. | |
| 6,442,410 B1 | 8/2002 | Steffes | |
| 6,881,198 B2 | 4/2005 | Brown | |
| 7,245,952 B2 | 7/2007 | Cameron | |
| 7,618,142 B2 | 11/2009 | Back | |
| 7,653,424 B2 | 1/2010 | March | |
| 8,380,270 B2 | 2/2013 | Menon | |
| 9,498,130 B2* | 11/2016 | Najafi | A61B 5/0215 |
| 9,772,301 B2* | 9/2017 | Kim | H01L 29/24 |
| 2006/0183986 A1 | 8/2006 | Rice et al. | |
| 2007/0004975 A1 | 1/2007 | Zribi et al. | |
| 2008/0103376 A1 | 5/2008 | Felder | |
| 2010/0113901 A1 | 5/2010 | Zhang | |
| 2010/0213057 A1* | 8/2010 | Feldman | G01N 27/3274 204/403.14 |
| 2011/0270022 A1 | 11/2011 | Honaryar et al. | |
| 2012/0162600 A1* | 6/2012 | Pugh | G02C 7/04 351/159.03 |
| 2012/0226133 A1* | 9/2012 | Wong | A61B 5/6846 600/398 |
| 2012/0245444 A1 | 9/2012 | Otis et al. | |
| 2012/0302861 A1* | 11/2012 | Marshall | A61F 9/00781 600/398 |
| 2013/0090534 A1 | 4/2013 | Burns et al. | |
| 2014/0275923 A1* | 9/2014 | Haffner | A61B 3/16 600/377 |
| 2014/0290054 A1 | 10/2014 | Etzkorn | |
| 2014/0296674 A1 | 10/2014 | Etzikom | |
| 2014/0343387 A1 | 11/2014 | Pugh et al. | |
| 2015/0087945 A1 | 3/2015 | Ziaie et al. | |
| 2016/0000325 A1* | 1/2016 | Cao | A61B 5/6839 600/398 |
| 2018/0333085 A1 | 11/2018 | Martin et al. | |

FOREIGN PATENT DOCUMENTS

| | | | |
|---|---|---|---|
| WO | WO-0116575 A1 * | 3/2001 | ............ A61B 5/1486 |
| WO | WO 2017/004531 | 1/2017 | |

OTHER PUBLICATIONS

International Search Report in International Application No. PCT/US2018/063796 dated Feb. 5, 2019, 2 pages.

McNichols et al., "Development of a Non-invasive Polarimetric Glucose Sensor," IEEE Photonics Society [online] Apr. 1998 [retrieved on Oct. 20, 2015]. Retrieved from the Internet:<URL:http://photonicssociety.org/newsletters/apr98/glucosesensor.htm>, 3 pages.

EP Extended Search Report in European Appln. No. 18888956.2, dated Aug. 11, 2021, 9 pages.

* cited by examiner

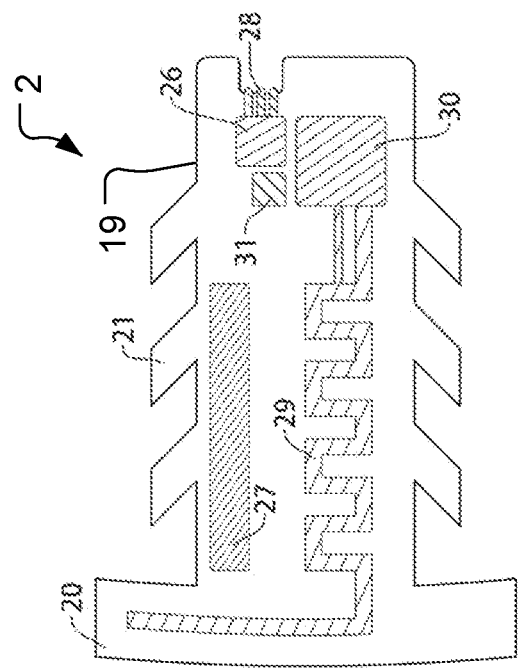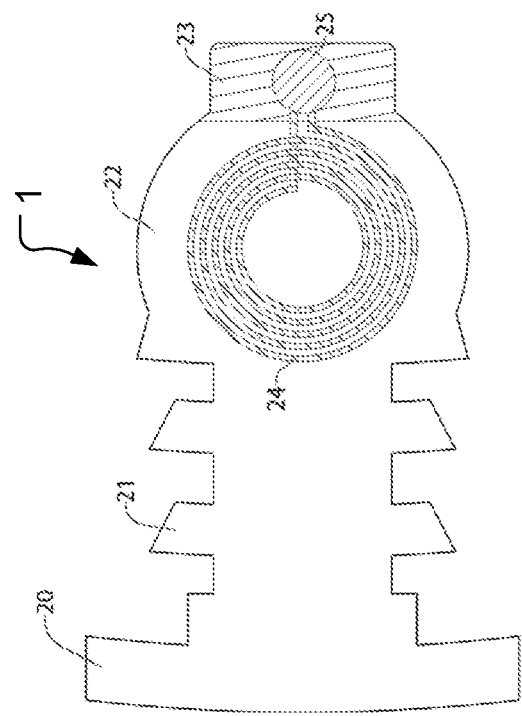
Fig. 1a
Fig. 1b
Fig. 2

IMPLANTABLE OCULAR GLUCOSE SENSOR DEVICES AND METHODS

CROSS-REFERENCE TO RELATED APPLICATIONS

This application claims the benefit of U.S. Provisional Application Ser. No. 62/597,156, filed Dec. 11, 2017. The disclosure of the prior application is considered part of (and is incorporated by reference in) the disclosure of this application.

BACKGROUND

1. Technical Field

This document relates to devices for glucose monitoring. For example, this document relates to implantable ocular glucose sensor devices that measure the glucose concentration of aqueous humor of the eye.

2. Background Information

The World Health Organization (WHO) estimated 412 million adults were afflicted with diabetes in 2014, and consequently identified diabetes as the 8th leading cause of death worldwide. Moreover, the prevalence of diabetes is predicted to significantly increase due to population aging, urbanization, and obesity.

Diabetes mellitus refers to a group of chronic metabolic disorders causing elevated blood glucose levels over a prolonged period. Rapid and severe elevations in blood glucose can lead to life-threatening medical emergencies such as diabetic ketoacidosis and hyperglycemic hyperosmolar state. Chronically elevated blood glucose over many years is associated with damage to the blood vessels and complications of diabetes. Damage to small blood vessels, or microangiopathy, is associated with diabetic nephropathy, retinopathy, and neuropathy. Damage to the large vessels, or macroangiopathy, is associated with cardiovascular disease, heart attack, and stroke.

A wide body of research has shown the complications of diabetes are less prevalent and severe in individuals with well-controlled blood glucose. Blood glucose (BG) testing is currently performed by piercing the skin (typically, on the finger) to draw blood, then applying the blood to a chemically active disposable 'test-strip' that is read in an electrical device called a point of care (POC) glucometer. A wide body of diabetes literature has associated improved treatment outcomes with both increased frequency of POC glucometer checks and use of continuous glucose monitoring (CGM) technology.

SUMMARY

This document describes devices for glucose monitoring. For example, this document describes implantable ocular glucose sensor devices that continuously measure the glucose concentration of aqueous humor of the eye. In some examples, the ocular glucose sensors described herein include a biocompatible housing; a sensor by which to measure a concentration of glucose; and a transmitter by which to communicate with an external device. In some cases, the device can be implanted at least partially within the anterior chamber in order to access aqueous humor. In some implementations, a protruding portion of the device may be externalized through the sclera. Optionally, the protruding portion may be covered with conjunctiva tissue to reduce the potential for infection.

Traditional interstitial CGM technology is disposable and requires insertion of a sensor filament just beneath the skin to be held in place with adhesive material. Re-insertion of a new sensor filament is required approximately every 7-14 days. A significant proportion of individuals are therefore unable to tolerate due to adverse skin and sensitivity reactions. Others are unable to tolerate due to frequent and complicated insertion procedures that necessitate repeated self-injury and can sometimes cause users significant pain. Others cannot tolerate the cosmetic appearance and or sensation of a foreign object on their body. Others lack adequate subcutaneous tissue for sensor insertion due to a slender body habitus.

There have been some recent research and/or commercial endeavors to create a smart contact lens capable of determining BG concentrations by measuring and correlating BG to aqueous tear film glucose concentrations. To date, such projects have been in large part impractical due to several challenges, such as an insufficient correlation between tear glucose levels and BG levels. An alternative approach is described herein, wherein aqueous humor is measured to correlate BG concentrations. Recent research has demonstrated aqueous humor glucose concentration is strongly correlated to BG concentration in both absolute value and dynamics. Thus, continuous glucose monitoring of aqueous humor is useful for medical decision-making purposes.

Implementations can include any, all, or none of the following features.

In one aspect, this disclosure is directed to an implantable ocular glucose sensor device that includes: (i) a biocompatible housing configured to be implanted at least partially in an anterior chamber of an eye; (ii) a sensor for measuring a concentration of glucose in aqueous humor of the eye, the sensor disposed at least partially within an interior space defined by the biocompatible housing; and (iii) communication circuitry for wirelessly communicating measured glucose concentrations of the aqueous humor to an external device. The communication circuitry is in electrical communication with the sensor and disposed at least partially within the interior space defined by the biocompatible housing.

Such an implantable ocular glucose sensor may optionally include one or more of the following features. The biocompatible housing may be thermoplastic polyurethane film. The biocompatible housing may be injection molded over the sensor and communication circuitry. The sensor may comprise a three-electrode electrochemical system that includes a working electrode, a counter electrode, and a reference electrode. The working electrode may be modified with glucose oxidase. The working electrode may be modified with glucose dehydrogenase. The working electrode may contain a nanostructured metal-oxide layer. The sensor may comprise a two-electrode electrochemical system including a working electrode and a dual counter or reference electrode. The working electrode may be modified with glucose oxidase. The working electrode may be modified with glucose dehydrogenase. The working electrode may contain a nanostructured metal-oxide layer. The device communication circuitry may comprise an inductor. The inductor may be connected to a rectifier and used to power the sensor. The communication circuitry may comprise an RF antenna. The sensor may be powered by a thin film battery disposed within the biocompatible housing.

In another aspect, this disclosure is directed to an implantable ocular glucose sensor device that includes: (a) a biocompatible housing configured to be implanted at least partially in an anterior chamber of an eye; (b) a polymer layer disposed at least partially within an interior space defined by the biocompatible housing, at least a portion of the polymer layer exposed to aqueous humor of the eye while the device is implanted in the eye, the polymer layer comprising a material that changes volume in response to varying glucose concentrations of the aqueous humor; (c) a pressure sensor disposed at least partially within the interior space defined by the biocompatible housing and abutting the polymer layer; and (d) communication circuitry for wirelessly communicating pressure signals from the pressure sensor to an external device. The communication circuitry is in electrical communication with the pressure sensor and disposed at least partially within the interior space defined by the biocompatible housing.

Such an implantable ocular glucose sensor device may optionally include one or more of the following features. The polymer layer may comprise boronic acid or a boronic acid derivative. The polymer layer may be covered by a glucose permeable membrane. The communication circuitry may comprise an inductor. The inductor may form a passive LC resonator with the pressure sensor. The passive LC resonator may transmit glucose concentration to an external antenna through a change in resonant frequency.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1a is a top view of an example implantable ocular glucose sensor utilizing a capacitive pressure sensor disposed over a volume-responsive polymer hydrogel in accordance with some embodiments.

FIG. 1b is a side view of the implantable ocular glucose sensor of FIG. 1a.

FIG. 2 is a top view of an example implantable ocular glucose sensor utilizing an onboard thin-film battery which powers a microcontroller, a three-electrode amperometric glucose sensor, and an RF antenna, in accordance with some embodiments.

Like reference numbers represent corresponding parts throughout.

DETAILED DESCRIPTION

Figure 3:
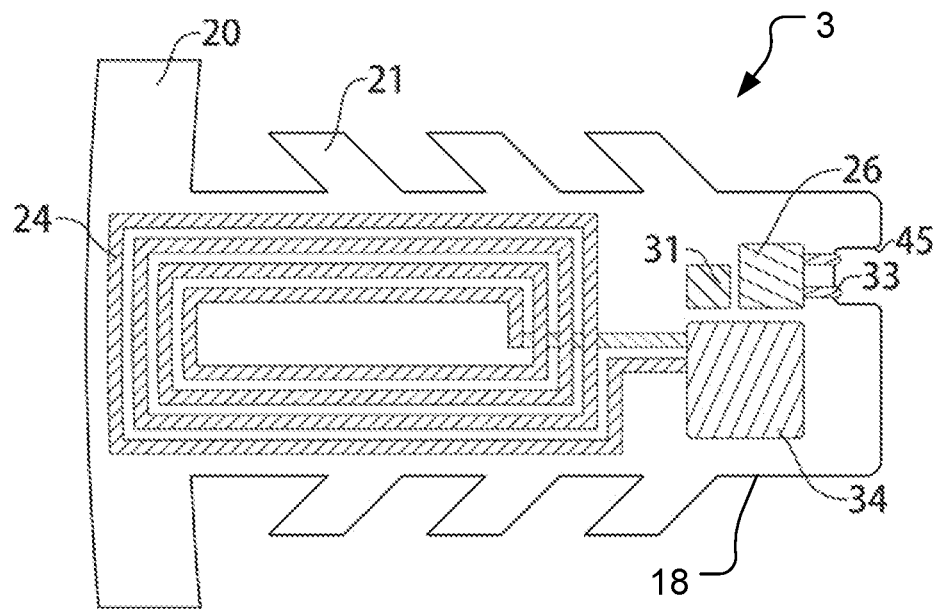
FIG. 3 is a top view of an example implantable ocular glucose sensor powered by external energy through an inductor. The sensor includes a rectifier with an impedance matching network and a two-electrode electrochemical glucose sensor, in accordance with some embodiments.

This document describes devices for glucose monitoring. For example, this document describes implantable ocular glucose sensor devices that continuously measure the glucose concentration of aqueous humor of the eye. The present disclosure broadly describes and encompasses implantable ocular glucose sensor devices which are at least partially located within the anterior chamber.

FIG. 1a is a top view of a first example embodiment of an implantable ocular glucose sensor device 1. FIG. 1b is a side view of the implantable ocular glucose sensor device 1. The implantable ocular glucose sensor device 1 (or simply "device 1") includes a biocompatible housing 22, a glucose-sensitive hydrogel 23, a MEMS pressure sensor 25, and an inductor 24 (or coil 24).

The glucose-sensitive hydrogel 23, the MEMS pressure sensor 25, and the inductor 24 are each disposed within an interior space defined by the housing 22. For example, in the depicted embodiment the housing 22 includes a first outer layer and a second outer layer (between which the interior space is defined). However, at least some of the glucose-sensitive hydrogel 23 at the distal end of the device 1 (on the right hand side of FIGS. 1a and 1b) is not covered by the housing 22. Accordingly, the glucose-sensitive hydrogel 23 is thereby exposed to aqueous humor of an eye while the device 1 is implanted in the eye (e.g., refer to FIGS. 5 and 6).

The MEMS pressure sensor 25 can be abutted in direct contact with the glucose-sensitive hydrogel 23. Therefore, while the device 1 is implanted in an eye, glucose-sensitive hydrogel 23 is in contact with the aqueous humor in the eye, and the MEMS pressure sensor 25 is in contact with the glucose-sensitive hydrogel 23.

The glucose-sensitive hydrogel 23 changes volume in response to changes in glucose concentrations of the aqueous humor in contact with the distal end of the device 1 (where the glucose-sensitive hydrogel 23 is exposed to and in contact with the aqueous humor). Volume changes of the glucose-sensitive hydrogel 23 (in response to changes in glucose concentrations of the aqueous humor) cause corresponding changes in the pressure exerted by the glucose-sensitive hydrogel 23 on the MEMS pressure sensor 25. Put simply, the MEMS pressure sensor 25 can indicate glucose concentrations of the aqueous humor because the volume of the glucose-sensitive hydrogel 23 is responsive to glucose concentration.

Electrically, the MEMS pressure sensor 25 is connected (e.g., in series) with an inductor 24, thereby forming a passive LC circuit (inductor-capacitor circuit). That is, the depicted device 1 does not include an on-board power source.

When the MEMS pressure sensor 25 detects changes in the glucose concentrations of the aqueous humor (e.g., via the glucose-sensitive hydrogel 23 as described above), the resonant frequency of the LC circuit (comprised of MEMS pressure sensor 25 and inductor 24) changes correspondingly. That change of resonant frequency can be detected by an external device, and then converted to one or more signals that correlate the resonant frequency to a glucose reading indicative of the glucose concentration of the person's aqueous humor in which the device 1 is implanted.

In some cases, the external device used to determine the resonant frequency of the LC circuit (comprised of MEMS pressure sensor 25 and inductor 24) comprises an external coil and associated circuitry that can be inductively coupled with the inductor 24 to establish wireless communications there between. Such an external coil and circuitry can be incorporated in various types of devices such as, but not limited to, eyeglasses, an attachment to a mobile device (e.g., a smart phone), a dedicated portable glucose detector device, and the like. In some cases, the inductive coupling (wireless communication) between the LC circuit and the external coil can be on-going (e.g., using eyeglasses). In some cases, the inductive coupling of the LC circuit and the external coil can be established on an as-needed basis (e.g., by the person placing a device in close proximity to the device 1 while it is implanted in the person's eye).

Figure 6:
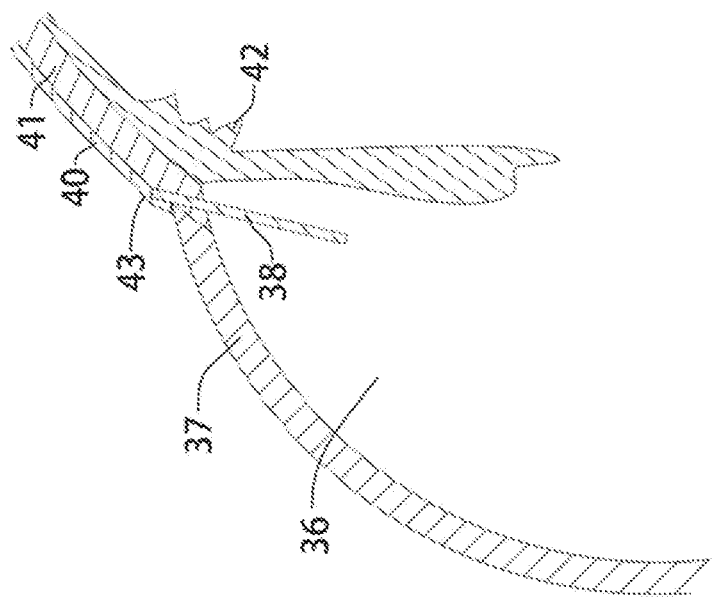
FIG. 6 is an anatomical depiction of an eye demonstrating placement of an example device through the sclera with a layer of conjunctiva tissue placed over the crossbar tab of the device.
Figure 5:
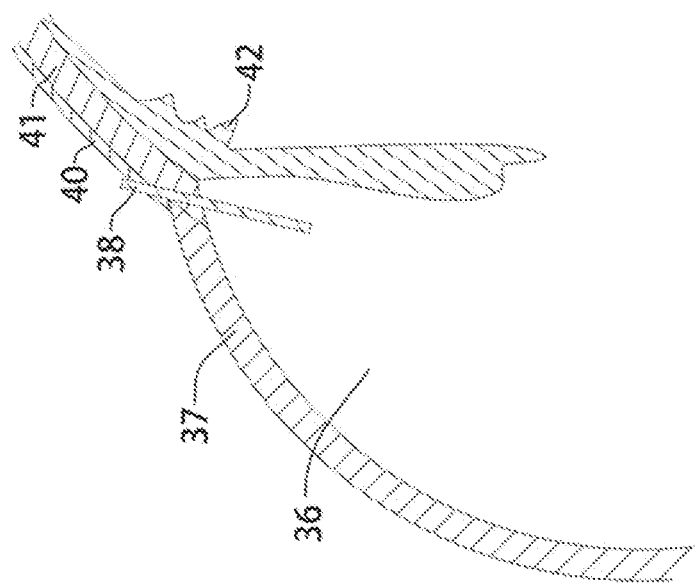
FIG. 5 is an anatomical depiction of an eye demonstrating placement of an example device through the sclera located partially within the anterior chamber.

When implanted, the body or housing 22 of the device 1 is anchored and immobilized within the anterior chamber 36 (e.g., see FIGS. 5 and 6). The housing 22 can include one or more lateral protrusions 21, which help to anchor the device 1 to the surrounding sclera 41 and conjunctiva tissue 40, thereby providing migration resistance.

In some cases, the device 1 can be implanted through a keratome blade stab incision which is shorter than a crossbar tab 20 located at a proximal end of the device 1. Accordingly, in some cases, the crossbar tab 20 is located outside the anterior chamber 36, and thereby prevents the device 1 from being inserted too far into an eye.

FIG. 2 is a top view of another example embodiment of an implantable ocular glucose sensor device 2. The device 2 includes a biocompatible housing 19, a thin film battery 27, a three-electrode electrochemical glucose sensor 28, an op amp 26, a DC-DC converter 31, a microcontroller 30, and an RF antenna 29. As with device 1, the housing 19 of the device 2 defines an interior space within which the aforementioned components are housed, except for the three-electrode electrochemical glucose sensor 28 which is at least partially exposed at the distal end of the device 2 by protruding therefrom. Accordingly, the three-electrode electrochemical glucose sensor 28 is exposed to and arranged to make contact with aqueous humor of an eye while the device 2 is implanted in the eye (e.g., refer to FIGS. 5 and 6).

In some embodiments, the three-electrode electrochemical glucose sensor 28 includes a working electrode, reference electrode, and counter electrode. The working electrode can be modified with a sensing enzyme capable of converting glucose to glucolactone. In at least some embodiments, the sensing enzyme is glucose oxidase, glucose dehydrogenase, or other suitable enzymes.

In operation, the three-electrode electrochemical glucose sensor 28 is powered by the thin film battery 27 (via the DC-DC converter 31 and the op amp 26). Voltage is applied between two of the electrodes of the three-electrode electrochemical glucose sensor 28 (e.g., between the working electrode and the reference electrode). Glucose from the aqueous humor of the eye in which the device 2 is implanted will oxidize at the working electrode in response to the voltage. The oxidation will generate a current that is proportional to the glucose concentration of the aqueous humor. The microcontroller 30 receives the current signal as an input and facilitates an output signal that is wirelessly transmitted to an external device over the RF antenna 29. Various types of external devices can receive the wirelessly transmitted output signal. Such external devices can include, but are not limited to, a mobile device (e.g., a smart phone), a dedicated portable glucose detector device, eyeglasses, earrings, headband, other wearable devices, and the like.

In some embodiments, the device 2 uses Bluetooth as its wireless communication technology. In some cases, other short-range wireless communication technologies are used such as, but not limited to, infrared (IR), radio frequency (RF), Wi-Fi, ANT+, radio-frequency identification (RFID), near-field communications (NFC), IEEE 802.15.4, and IEEE 802.22.

In some embodiments, the antenna 29 is arranged relative to the housing 19 such that at least a portion of the antenna 29 is outside of the eye in which the device 2 is implanted. For example, in the depicted embodiment a portion of the antenna 29 extends into the crossbar tab 20 (which is located outside the anterior chamber 36 of an eye while the device 2 is implanted in the eye). Such an arrangement can be advantageous because transmissions travel through air more readily than through liquid (such as aqueous humor).

When implanted, the body or housing 19 of the device 2 is anchored and immobilized within the anterior chamber 36 (e.g., see FIGS. 5 and 6). The housing 19 can include one or more lateral protrusions 21, which help to anchor the device 2 to the surrounding sclera 41 and conjunctiva tissue 40, thereby providing migration resistance.

In some cases, the device 2 can be implanted through a keratome blade stab incision which is shorter than a crossbar tab 20 located at a proximal end of the device 2. Accordingly, in some cases, the crossbar tab 20 is located outside the anterior chamber 36, and thereby prevents the device 2 from being inserted too far into an eye.

Figure 4:
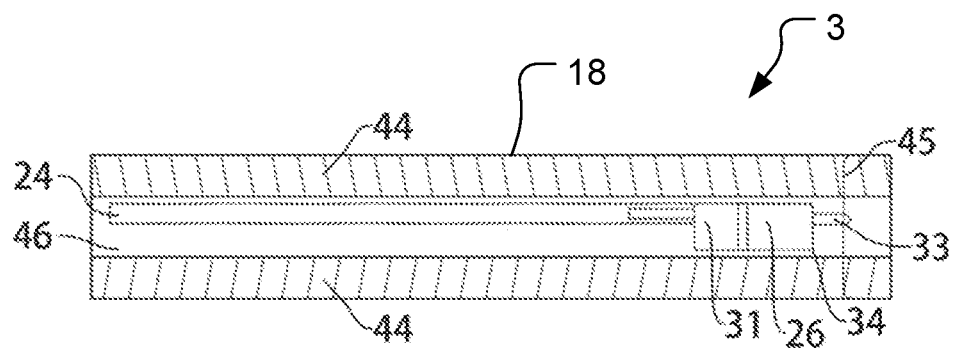
FIG. 4 is a side view of the embodiment described in FIG. 3. The sensing electronics are disposed between two layers of polyurethane film, and embedded within a polymer matrix with known biocompatibility.

FIG. 3 is a top view of a first example embodiment of an implantable ocular glucose sensor device 3. FIG. 4 is a side view of the implantable ocular glucose sensor device 3. The device 3 includes a biocompatible housing 18, a two-electrode electrochemical glucose sensor 33, a set of operational amplifiers 26, a DC-DC converter 31, a microcontroller/rectifier 34, and an inductor 24.

As with devices 1 and 2, the housing 19 of the device 3 defines an interior space within which the aforementioned components are housed, except for the two-electrode electrochemical glucose sensor 33 which is at least partially exposed at the distal end of the device 3 by protruding therefrom. In the depicted embodiment, the distal end of the device 3 contains a small cutout 45 which allows fluid communication between the aqueous humor of the anterior chamber 36 (e.g., see FIGS. 5 and 6), and the electrodes 33 of the electrochemical system. Accordingly, the two-electrode electrochemical glucose sensor 33 is exposed to and arranged to make contact with aqueous humor of an eye while the device 3 is implanted in the eye (e.g., refer to FIGS. 5 and 6).

The device 3 is inductively powered. There is no on-board battery. Instead, power is inductively transmitted to the device 3 via an external coil that is coupled with the inductor 24. The external coil can also receive signals from the inductor 24 that are indicative of the measured glucose concentration. Such an external coil can be a part of any suitable external device such as, but not limited to, a mobile device (e.g., a smart phone), a dedicated portable glucose detector device, eyeglasses, other wearable devices, and the like. In some cases, the device with the external coil is temporarily held by a user closely to the user's eye in order to power the device 3 and to receive one or more glucose concentration readings from the device 3. In some cases, the device with the external coil is coupled to the inductor 24 on a relatively constant, on-going basis (such as by including the external coil in a pair of eyeglasses). The inductor 24 coils extend into the crossbar tab 20 region, which can increase the quality factor during resonant analysis.

When implanted, the body or housing 18 of the device 3 is anchored and immobilized within the anterior chamber 36 (e.g., see FIGS. 5 and 6). The housing 18 can include one or more lateral protrusions 21, which help to anchor the device 3 to the surrounding sclera 41 and conjunctiva tissue 40, thereby providing migration resistance.

In some cases, the device 3 can be implanted through a keratome blade stab incision which is shorter than a crossbar tab 20 located at a proximal end of the device 3. Accordingly, in some cases, the crossbar tab 20 is located outside the anterior chamber 36, and thereby prevents the device 3 from being inserted too far into an eye.

In some cases, as in FIG. 1-4, electrical components, such as the operational amplifier 26, DC-DC converter 31, and microcontroller/rectifier 34, are physically separated, however the various electrical components may also be combined on a single integrated circuit and embedded directly within a biocompatible housing. An integrated circuit with all components incorporated during fabrication may have a smaller footprint than the individual components would separately, and thus produce a smaller implantable glucose sensor.

FIG. 5 is a depiction of a first example implantation technique of an example device 38 (which is representative of any of the device embodiments described herein) implanted in an inner eye and anterior chamber 36. In some embodiments, the device 38 is inserted through a stab incision of the sclera 41 and conjunctiva 40. The aperture of the incision can be angled such that the device 38 points towards the cornea 37 and does not touch the iris, lens, or ciliary body 42. In this exemplary implantation technique, the proximal end crossbar tab 20 (refer to FIGS. 1-4) prevents the device 38 from being inserted too far, and the lateral protrusions 21 help anchor the device 38 to the surrounding sclera 41 and conjunctiva tissue 40.

FIG. 6 is a depiction of a second example implantation technique of the example device 38 implanted in the inner eye and anterior chamber 36. The device 38 is inserted through a stab incision of the sclera 41. In this exemplary implantation technique, conjunctiva tissue 43 is excised from the insertion site and subsequently used to cover 43 the crossbar tab 20 (refer to FIGS. 1-4) following insertion. The aperture of the incision is angled such that the device points towards the cornea 37 and does not touch the iris, lens, or ciliary body 42. The proximal end crossbar tab 20 (refer to FIGS. 1-4) prevents the device 38 from being inserted too far, and the lateral protrusions 21 help anchor the device 38 to the surrounding sclera 41 and conjunctiva tissue 40.

Biocompatible Housings (Additional Details)

The biocompatible housings of the devices described herein are intended for long-term implantation and must be able to withstand the harsh environment of the body. There are a vast number of biomaterials suitable for implantation, including but not limited to metals, ceramics, polymers, and composite materials. All of these material types may be used to fabricate the biocompatible housing of an implantable ocular glucose sensor as described herein. Polymers will be discussed in greater detail since they exhibit easy fabrication, as well as a wide range of compositions and subsequent material properties.

In polymers, the host may potentially cause several issues including protein adsorption, cell adhesion, device encapsulation, device calcification, swelling, hydrolysis, oxidation, wear, and release of certain moieties. Alternatively, in tissue the presence of polymer may potentially cause thrombosis, inflammation, fibrous encapsulation, osteolysis, leachables or migration of polymer additives which can cause hemolysis, toxicity, sensitization, mutagenicity, or carcinogenicity. Consequently, it is important to consider all of these issues when selecting a suitable biocompatible housing for an implantable ocular glucose sensor. It is also important to test the relevant material under biological conditions either through a bench model, or more directly with animal studies. Physical properties such as mechanical strength (tensile, compressive, fatigue, etc.) as well as transport properties, degradation rate and byproducts, surface properties including chemistry, morphology, and roughness, as well as biological interactions should all be considered. Process and design considerations are also important in selecting the optimal biocompatible housing material.

Several polymers are well-suited for the biocompatible housing of the current invention including but not limited to polyurethanes, silicones, fluoropolymers, and polyethylenes. A particularly useful polymer to be used as the biocompatible housing is thermoplastic polyurethane, which can either be used as a premanufactured polymer film, or injection molded.

The biocompatible housing may optionally contain lateral protrusions intended to anchor the device within the tissue of the eye. Such structures may take many forms, but should focus on increasing the effective surface area of the portion of the device which contacts tissue. Some or all of the biocompatible housing may optionally be chemically or physically modified to improve the bonding characteristics of the material/body interface. Such modifications may include but are not limited to plasma treatment, chemical anchoring through surface moieties, or surface roughening.

The biocompatible housing can be roughly between 0.5 mm and 10 mm in its longest dimension, but ideally between 2 mm and 5 mm in length. The largest width of the device can be between 0.25 mm and 5 mm, but ideally between 1 mm and 2 mm in width. The crossbar tab 20 is intended to be externalized with respect to the anterior chamber, and may optionally be covered with an excised portion of conjunctiva tissue 43 as in FIG. 6. The crossbar tab 20 should be larger in width than the keratome blade used to make the stab incision to ensure that the device cannot be inserted past the crossbar tab 20.

In at least some of the embodiments, the biocompatible housing is designed to match the modulus of the surrounding tissue of the sclera.

In at least some of the embodiments, the biocompatible housing is composed of thermoplastic polyurethane film. A laminate is created in which the requisite electrical components have been disposed within two layers of thermoplastic polyurethane film. The electrical components may optionally be sealed in parylene prior to inclusion within the laminate.

An inner layer of the laminate 46 (e.g., refer to FIGS. 1*b* and 4) surrounding the electrical components is composed of a polymer with known biocompatibility. A useful polymer to be used as the inner layer 46 is a network polymer composed of poly(ethylene glycol) monomer and a suitable photoinitiator or thermal-initiator. A prepolymer solution can be mixed containing the monomer and the photoinitiator or thermal initiator. The prepolymer solution is placed on the surface of a sheet of polyurethane film, the electrical components are placed within the prepolymer solution and a sheet of polyurethane film is placed over the prepolymer solution and electrical components. The prepolymer solution is then subjected to UV radiation or heat to initiate polymerization. The final device may be perforated from this laminate by die-cutting, laser processing, or any other process capable of singulating devices with high fidelity. Poly (ethylene glycol) is known to exhibit excellent biocompatibility and also exhibits strong anti-biofouling properties which will prevent the adsorption of molecules, proteins, and ions onto its surface. Chain length of the inner layer 46 monomer should be chosen to minimize swell in in vivo conditions. Smaller chain lengths and increasing crosslink density will generally decrease swell ratio. A prepolymer solution may contain a single monomer, or a combination of monomers, or a combination of the monomer lengths. The composition of the monomer can be optimized to fine tune the material properties of the inner layer 46.

The sensor is intended to be implanted for at least 1 month, but may be functional after years of implantation. If the sensor becomes dysfunctional at any point, explantation will be required. The explantation procedure is minimal however, and a new sensor may be implanted in the same day if necessary.

Glucose Measurement (Additional Details)

Some embodiments described herein include a two-electrode or three-electrode sensing element, which interfaces with a potentiostat. A three-electrode system is comprised of a working electrode, a counter electrode, and a reference electrode. The working electrode is generally modified with a sensing enzyme, wherein the most commonly used enzyme is glucose oxidase, but may also be glucose dehydrogenase. In both cases, the enzyme is able to react with glucose to produce glucolactone. The enzyme operates with a cofactor which is reduced by the enzyme in proportion to the amount of glucolactone produced. The cofactor is then oxidized at the working electrode to produce a current which is quantified to determine the glucose concentration. A potentiostat controls the voltages associated with each electrode. Voltage is applied between the working and reference electrode, and current is measured between working and the reference electrode. The counter electrode maintains a constant voltage within the system by providing current in proportion to the current traveling out of the system through the working electrode.

The two-electrode system utilizes a combination reference/counter electrode. In general, three-electrode systems is likely to be more accurate since voltage is referenced to a constant value provided by the reference electrode. In the two-electrode system the counter electrode also serves as the reference electrode, wherein the counter electrode may change potential during the measurement, skewing results slightly. The error introduced by this potential change may insignificant compared to the signal of interested and will not affect the overall accuracy of the glucose measurement. In such cases, it is advantageous to use a two-electrode system as it reduces manufacturing complexity.

Any system utilizing a sensing enzyme may also optionally include various mediator chemicals to alter the electron transfer mechanisms of the system. In one such embodiment, an artificial electron mediator such as ferricyanide, hydroquinone, or ferrocene may be included to increase the electron transfer rate between the electrode and the sensing enzyme.

Another method of measuring glucose concentration in conjunction with some embodiments described herein is through a nonenzymatic nanostructured metal-oxide including but not limited to ZnO, Cu(I)/(II) oxides, $MnO_2$, $TiO_2$, $CeO_2$, $SiO_2$, or $ZrO_2$. These sensors may function under various operating principles including but not limited to potentiometric, amperometric, or conductometric. In one such embodiment, a nonenzymatic glucose sensor is created by electrospinning copper oxide nanofibers on a glassy carbon electrode. The electrode is measured amperometrically against a reference electrode wherein the current produced is proportional to the glucose concentration.

Another method of measuring glucose includes the use of a glucose-sensitive polymer which changes volume in response to varying glucose concentrations. In once such embodiment depicted in FIGS. 1a and 1b, a volume changing polymer 23 can be measured with an embedded MEMS pressure sensor 25 which is disposed within the biocompatible housing 22 of the sensor device 1. The MEMS pressure sensor 25 is connected in series with an inductor 24 to form a passive LC resonator which alters resonant frequency in response to glucose concentrations. In such an embodiment, the glucose-sensitive polymer may comprise a polymer which contains boronic acid, or a boronic acid derivative such as a phenylboronic acid. Phenylboronic acid modified hydrogel matrices have been shown to swell or shrink in the presence of glucose, which can be used as a means by which to measure glucose concentrations.

In at least some of the embodiments, the means by which to measure a concentration of glucose comprises a three-electrode system 28, including a working electrode, reference electrode, and counter electrode, embedded within a biocompatible housing. In some embodiments, a small opening 45 is defined in the biocompatible housing through which fluid can communicate with the three electrodes. The working electrode is modified with a sensing enzyme capable of converting glucose to glucolactone. In at least some embodiments, the sensing enzyme is glucose oxidase, or glucose dehydrogenase.

In at least some of the embodiments, the means by which to measure a concentration of glucose comprises a two-electrode system comprising a working electrode and a dual reference/counter electrode. The working electrode is modified with a sensing enzyme capable of reacting with glucose to produce glucolactone. In at least some embodiments, the sensing enzyme is glucose oxidase, or glucose dehydrogenase.

In at least some of the embodiments, the means by which to measure a concentration of glucose comprises an electrode system wherein at least one of the electrodes is modified with a metal-oxide layer capable of reacting selectively with glucose.

In at least some of the embodiments, the means by which to measure a concentration of glucose comprises an electrode system wherein at least one of the electrodes is modified with a metal-oxide layer capable of reacting selectively with glucose, such as copper oxide, zinc oxide, titanium dioxide, manganese dioxide, cerium dioxide, silicon dioxide, or zirconium oxide. The oxide layer may contain different nanostructures which help facilitate the reaction with glucose. The metal-oxide based electrode system may operate under a number of principles, including but not limited to potentiometric, amperometric, or conductometric.

In at least some embodiments, the means by which to measure glucose concentration comprises a volume-responsive polymer 23 located in the tail-end of the sensor. In one such embodiment the volume-responsive polymer contains concanavalin A (Con A), a glucose-specific lectin known to reversibly bind with glucose while inducing volumetric changes in the polymer. In another such embodiment, the responsive secondary polymer comprises a polymer composed at least partially of boronic acid, which also reversibly binds glucose inducing volumetric changes in the polymer. An example of one such polymer is Poly(N-hydroxyethyl acrylamide)-ran-3-acrylamidophenylboronic acid (PHEAA-ran-PAAPBA). In either of the described embodiments, the volume-responsive polymer is disposed under a MEMS pressure sensor which can detect changes in volume of the polymer. The pressure sensor may optionally be capacitive-based wherein the capacitor is connected in series to an inductor to create a passive LC tank resonator.

External Communication (Additional Details)

The implantable ocular glucose sensor devices described herein are able to communicate with an external device to convey at least glucose concentration information. This can be accomplished either passively as in the embodiment depicted in FIGS. 1a and 1b, or actively as in the embodiments depicted in FIG. 2-4. In a passive system, the means by which to measure glucose may comprise a sensing modality which acts as the R or C of an RLC (resistor-inductor-capacitor) network, such as a conductimetric electrode, a capacitive MEMS pressure sensor 25, or a poteniometric metal oxide sensor. The energy received by the sensor from an external device is used to resonate the RLC network, where the reflecting signal can be used to quantify certain parameters of the system. For example, in the embodiment described in FIGS. 1a and 1b, incoming energy is passively radiated through the LC network which will eventually dampen to nothing due to inherent resistance of the components. The resonant frequency of the system is defined by the L and C of the network, and since the L is fixed, the capacitance of the embedded pressure sensor will ultimately determine the resonant frequency of the system. The capacitance of the pressure sensor is proportional to the glucose concentration, so any change in glucose can be passively communicated to the external device.

In an active system, incoming energy is converted from alternating current into direct current by means of a rectifier 34, or powered directly from an embedded battery 27. In one such embodiment described in FIG. 3, a rectifier 34 converts incoming energy into DC, and a DC-DC converter 31 is used to assure the proper voltage is used to power the integrated circuits. The power is used to operate a microcontroller, apply bias voltage to the electrode system through embedded operational amplifiers 26, and transmit concentration information to an external device through the RF antenna 29.

In at least some of the embodiments, the implantable ocular glucose sensor is powered externally through either inductive coupling, or highly resonant inductive coupling. The sensor may contain a rectifier 34 and a DC-DC converter 31 to convert electromagnetic radiation into DC power and alter the voltage to a set value. The sensor may also optionally contain a rectifier with impedance matching network 32 to improve quality factor of the implanted sensor, or an embedded temperature sensor to improve calibration results.

In at least some embodiments, the implant contains an embedded power source such as a thin film lithium ion battery 27. In one such embodiment depicted in FIG. 2, a microcontroller is powered by an embedded thin-film battery. The microcontroller uses an RF antenna 29 to communicate with an external device, sending signals with frequencies between 3 kHz and 300 GHz. The implant may contain a microcontroller 30 and the requisite electronics to power the various sensing modalities described herein.

In some cases, the external device may additionally generate audible and/or visual alerts based upon clinically relevant thresholds and or rapid changes in aqueous humor glucose concentration measurements. In some cases, the external device may additionally display sensor data. In some cases, the external device may additionally provide treatment decision support such as recommendations for insulin dosing and or carbohydrate intake. In some cases, the external device may additionally record and save aqueous humor glucose measurement data in a logbook format for later review. In some cases, the external device may additionally possess internet connectivity for the purpose of cloud data storage, remote monitoring, telemedicine and the like. In some cases, the external device may additionally possess wireless communication ability for integration with other devices and software platforms such as, but not limited to, insulin pumps, activity trackers, Apple Health, Google Fit, and the like.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An implantable ocular glucose sensor device, comprising:
   a biocompatible housing comprising: (i) a proximal end having a crossbar tab, (ii) a distal end that houses a sensor, and (iii) two or more pairs of lateral protrusions positioned between the proximal and distal ends,
   wherein the crossbar tab comprises a first rigid member and a second rigid member, wherein the first and second rigid members extend in opposite lateral directions, wherein the first and second rigid members each include a curved distal surface, the biocompatible housing configured to be implanted in an incision of a sclera of an eye such that: (i) the crossbar tab protrudes externally of the sclera, (ii) the curved distal surfaces of the first and second rigid members contact and conform with a curvature of the sclera, (iii) the two or more pairs of lateral protrusions are within the sclera to anchor the biocompatible housing to the sclera, and (iv) the sensor is at least partially in an anterior chamber of the eye;

the sensor for measuring a concentration of glucose in aqueous humor of the eye, the sensor disposed at least partially within an interior space defined by the biocompatible housing; and communication circuitry comprising an antenna or an inductor for wirelessly communicating measured glucose concentrations of the aqueous humor to an external device, the communication circuitry in electrical communication with the sensor and disposed at least partially within the interior space defined by the biocompatible housing, wherein at least a portion of the antenna or the inductor extends into the crossbar tab.

2. The device of claim 1, wherein the biocompatible housing is thermoplastic polyurethane film.

3. The device of claim 1, wherein the biocompatible housing is injection molded over the sensor and communication circuitry.

4. The device of claim 1, wherein the sensor comprises a three-electrode electrochemical system that includes a working electrode, a counter electrode, and a reference electrode.

5. The device of claim 4, wherein the working electrode is modified with glucose oxidase.

6. The device of claim 4, wherein the working electrode is modified with glucose dehydrogenase.

7. The device of claim 4, wherein the working electrode contains a nanostructured metal-oxide layer.

8. The device of claim 1, wherein the sensor comprises a two-electrode electrochemical system including a working electrode and a dual counter or reference electrode.

9. The device of claim 8, wherein the working electrode is modified with glucose oxidase.

10. The device of claim 8, wherein the working electrode is modified with glucose dehydrogenase.

11. The device of claim 8, wherein the working electrode contains a nanostructured metal-oxide layer.

12. The device of claim 1, wherein the communication circuitry comprises the inductor.

13. The device of claim 12, wherein the inductor is connected to a rectifier and used to power the sensor.

14. The device of claim 1, wherein the communication circuitry comprises an RF antenna.

15. The device of claim 1, wherein the sensor is powered by a thin film battery disposed within the biocompatible housing.

16. An implantable ocular glucose sensor device, comprising:

a biocompatible housing comprising: (i) a proximal end having a crossbar tab, (ii) a distal end having a polymer layer, and (iii) two or more pairs of lateral protrusions positioned between the proximal and distal ends, wherein the crossbar tab comprises a first rigid member and a second rigid member, wherein the first and second rigid members extend in opposite lateral directions, wherein the first and second rigid members each include a curved distal surface, the biocompatible housing configured to be implanted in an incision of a sclera of an eye such that: (i) the crossbar tab protrudes externally of the sclera, (ii) the curved distal surfaces of the first and second rigid members contact and conform with a curvature of the sclera, (iii) the two or more pairs of lateral protrusions are within the sclera to anchor the biocompatible housing to the sclera, and (iv) the sensor is at least partially in an anterior chamber of the eye;

the polymer layer disposed at least partially within an interior space defined by the biocompatible housing, at least a portion of the polymer layer exposed to aqueous humor of the eye while the device is implanted in the eye, the polymer layer comprising a material that changes volume in response to varying glucose concentrations of the aqueous humor;

a pressure sensor disposed at least partially within the interior space defined by the biocompatible housing and abutting the polymer layer; and communication circuitry comprising an antenna or an inductor for wirelessly communicating pressure signals from the pressure sensor to an external device, the communication circuitry in electrical communication with the pressure sensor and disposed at least partially within the interior space defined by the biocompatible housing, wherein at least a portion of the antenna or the inductor extends into the crossbar tab.

17. The device of claim 16, wherein the polymer layer comprises boronic acid or a boronic acid derivative.

18. The device of claim 16, wherein the polymer layer is covered by a glucose permeable membrane.

19. The device of claim 16, wherein the communication circuitry comprises the inductor.

20. The device of claim 19, wherein the inductor forms a passive LC resonator with the pressure sensor.

21. The device of claim 20, wherein the passive LC resonator transmits glucose concentration to an external antenna through a change in resonant frequency of the passive LC resonator.

* * * * *